United States Patent [19]

Brunke et al.

[11] Patent Number: 4,652,402
[45] Date of Patent: Mar. 24, 1987

[54] 4-(2,2,3-TRIMETHYLCYCLOPENT-3-EN-1-YL)-BUT-3-EN-1-OLS, METHODS FOR THEIR PRODUCTION AND USE AS ODORANTS

[75] Inventors: Ernst-Joachim Brunke; Claus-Hermann Kappey, both of Holzminden, Fed. Rep. of Germany

[73] Assignee: DRAGOCO, Gerberding & Co., GmbH, Fed. Rep. of Germany

[21] Appl. No.: 797,520

[22] Filed: Nov. 13, 1985

[30] Foreign Application Priority Data

Nov. 16, 1984 [DE] Fed. Rep. of Germany ....... 3441902

[51] Int. Cl.[4] .......................... A61K 7/46; C07C 35/06
[52] U.S. Cl. .................................................. 252/522 R
[58] Field of Search ...................... 252/522 R; 568/838

[56] References Cited
U.S. PATENT DOCUMENTS

| | | | |
|---|---|---|---|
| 4,052,341 | 10/1977 | Naipawer | 568/838 |
| 4,149,020 | 4/1979 | Kamath et al. | 568/838 |
| 4,173,585 | 11/1979 | Yoshidu | 252/522 R |
| 4,501,687 | 2/1985 | Martel et al. | 252/522 R |

Primary Examiner—Werren B. Lone
Attorney, Agent, or Firm—Robbins & Laramie

[57] ABSTRACT

The $\beta,\gamma$-unsaturated 2,2,3-trimethylcyclopent-3-enyl derivatives of formula I

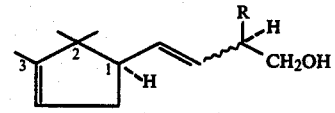

where R may be methyl, ethyl, propyl, isopropyl or butyl, the wavy line characterizes geometric isomers and the broken lines characterize stereoisomers. These compounds can be produced by reduction of the aldol condensation products of campholene aldehyde and aliphatic aldehydes using sodium borohydride at raised temperatures. The compounds can be used to individually or as a mixture with the relevant $\alpha,\beta$-unsaturated alcohols as odorants or as an ingredient of perfume oils for cosmetic and technical consumer goods.

17 Claims, 6 Drawing Figures $^1$H-NMR SPECTRUM (60 MHz, CCl$_4$) OF 22

FIG. 1: $^1$H-NMR SPECTRUM (60 MHz, CCl$_4$) OF 22

FIG. 2: MASS SPECTRUM OF 22 (E)

FIG. 3: MASS SPECTRUM OF 22 (Z)

FIG. 4: MASS SPECTRUM OF 4 (E)

FIG. 5: GAS CHROMATOGRAM (30 m DB WAX-30N; TEMPERATURE PROGRAM 100-240°C, 4°C/min.) OF REDUCTION MIXTURE AS PER EXAMPLE 1.

FIG. 6: GAS CHROMATOGRAM (30 m DB WAX-30N; TEMPERATURE PROGRAM 100-240°C, 4°C/min.) OF REDUCTION MIXTURE AS PER EXAMPLE 2

4-(2,2,3-TRIMETHYLCYCLOPENT-3-EN-1-YL)-BUT-3-EN-1-OLS, METHODS FOR THEIR PRODUCTION AND USE AS ODORANTS

BACKGROUND OF THE INVENTION

1. Field of the Invention

The present invention relates to 4-(2,2,3-trimethylcyclopent-3-en-1-yl)-but-3-en-1-ols, to their method of production, and to their use as odorants.

2. Description of the Prior Art

Derivatives of campholene aldehyde (1), a product of rearrangement of α-pinene epoxide are known as aroma chemicals of the sandalwood type (Survey: E.-J. Brunke and E. Klein, in: *Fragrance Chemistry*, ed. E. Theimer, Academic Press, New York, N.Y. 1982, pp. 424–26). For instance, the α,β-unsaturated aldehydes obtained by aldol condensation of camphene aldehyde (1) with acetone, propionic or butyraldehyde (catalyzed by alkali hydroxides or alcoholates), and the α,β-unsaturated alcohols 2, 3 and 4, obtained from the above by subsequent reduction have already been described in DE-A1 No. 992 391 as aroma chemicals with sandalwood and musk notes.

U.S. Pat. No. 4,052,341 describes the aldol condensation of camphene aldehyde (1) with methyl ketone (catalyzed by alkali hydroxides) to the α,β-unsaturated carbonyl compounds and their subsequent reduction to a mixture of the unsaturated secondary alcohols 5/6 and the saturated alcohols 7/8.

In U.S. Pat. No. 4,173,585, the aldol condensation of camphene aldehyde with various ketones using zinc acetate dihydrate is described. In contrast to the aldol condensations catalyzed with alkali hydroxides or alcoholates, it is not the uniform α,β-unsaturated ketones that are produced in this patent but rather mixtures of α,β- and β,γ-unsaturated ketones, which are present as (Z) and (E) isomers (9-12).

These mixtures are said to have fragrance notes of the ionone type (sweet, woody, green, melon-like, apricot-like, flowery, violet-like, ambrigris-like). The alcohol mixtures 14-16 obtained from the mixtures of the α,β- and β,γ-unsaturated ketones by reduction are said to possess sandalwood, cedarwood, resiny and flowery notes. The individual isomers were not isolated. Nothing is known about the odorous properties of the individual isomers.

SUMMARY OF THE INVENTION

The present invention is directed to 4-(2,2,3-trimethylcyclopent-3-en-1-yl)-but-3-en-1-ols of general formula I:

wherein R may be methyl, ethyl, propyl, isopropyl or butyl, the wavy line characterizes geometrical isomers and the broken lines characterize stereoisomers.

The compounds of formula I can be produced by reduction of the aldol condensation products of campholene aldehyde and aliphatic aldehydes using sodium borohydride at raised temperatures.

The compounds of formula I can be used individually or in a mixture with the relevant α,β-unsaturated alcohols as odorants or as an ingredient of perfume oils for cosmetic and technical consumer goods.

DETAILED DESCRIPTION OF THE INVENTION

We have now surprisingly found that the previously unknown β,γ-unsaturated alcohols of the general formula I possess characteristic woody-animal and soft-fruity odorous properties which differ substantially from the typical sandalwood or musk note of the α,β-unsaturated alcohols 3 or 4.

The odorous properties of the compounds of the general formula I are of advantage for their use as odorants, especially when combined with the relevant α,β-unsaturated alcohols of the same substitution.

β,γ-unsaturated alcohols of formula I can be prepared as shown in the following diagram and described below.

25

20

24

26

For the production of the β,γ-unsaturated alcohols of the general formula I camphene aldehyde (1) was likewise taken as a basis, being condensed in the known manner with short-chained aliphatic aldehydes, whereby the α,β-unsaturated aldehydes 17–20 were produced. Conditions for these aldol condensations have been described in DEA No. 1 922 391 and in U.S. Pat. No. 4,052,341, both of which are incorporated herein by reference. The reduction of the α,β-unsaturated aldehydes 17 and 18 to the corresponding α,β-unsaturated alcohols 3 and 4 can, according to DEA No. 1 922 391, incorporated herein by reference, be carried out with complex metal hydrides or in the presence of aluminum alcoholates according to the method of Meerwein-Pondorf.

We have now surprisingly found that when using complex hydrides, preferably sodium borohydride, in the presence of a basic medium, preferably soda lye, a partial deconjugation of the double bond from the α,β- to the β,γ-position takes place. The equilibrium that is established is influenced not only by the temperature and the reaction time, but also by the reduction of the carbonyl group to the alcohol group (Example 1, Table 1). Temperatures of 10°–80° C., preferably 30°–60° C., are utilized. From the mixtures produced, the compounds of formula I can be isolated by separation methods that are in themselves known, preferably by distillation.

Figure 1:
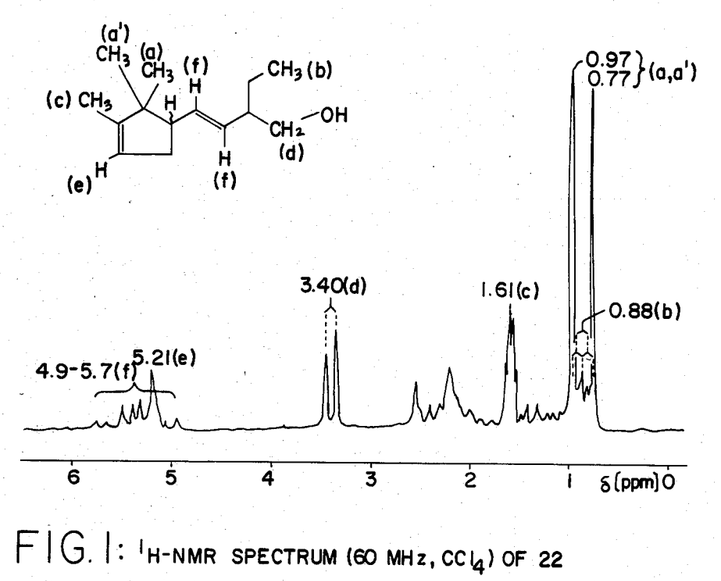
FIG. 1 shows the $^1$H-NMR spectrum of compound 22.
Figure 2:
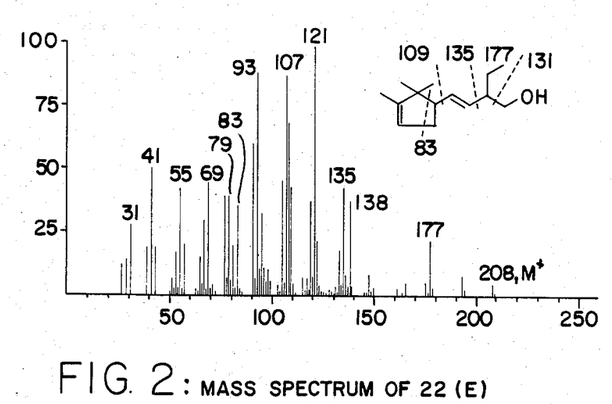
FIG. 2 shows the mass spectrum of the E isomer of compound 22.
Figure 3:
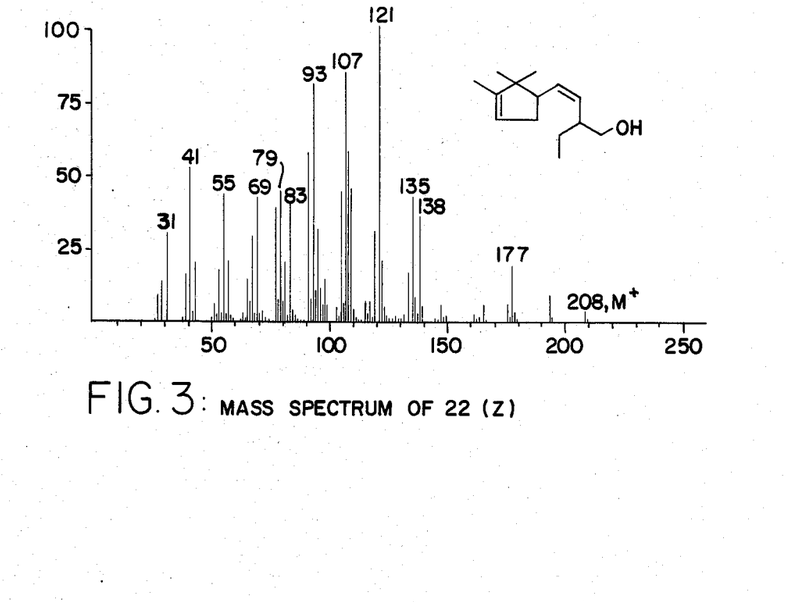
FIG. 3 shows the mass spectrum of the Z isomer of compound 22.
Figure 4:
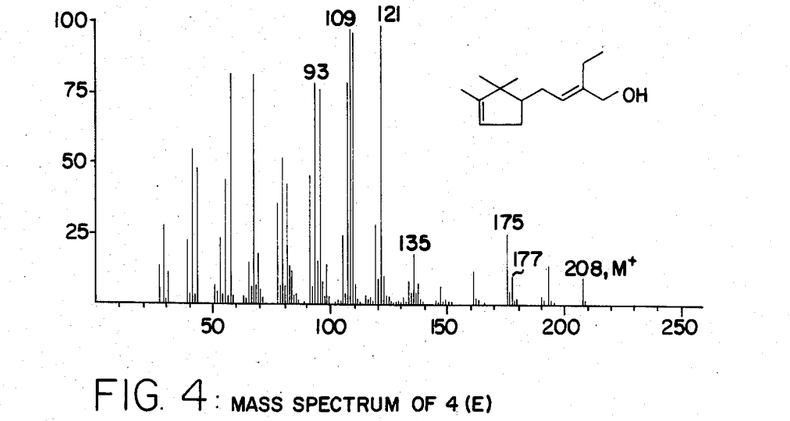
FIG. 4 shows the mass spectrum of the E isomer of compound 4.

The structure specified for the new compounds of the general formula I can be proved by spectroscopic methods. In the $^1$H-NMR spectrum (FIG. 1) of the isolated alcohol 22 there appears in addition to the signal for the olefinic proton of the cyclopentane system a multiplet at δ=4.9–5.7 ppm (2 protons) which characterizes the β,γ double bond in the side chain. This position of the double bond of 22 is likewise indicated by a strong IR band at 968 cm$^{-1}$ (disubstituted double bond). The mass-spectrometric fragmentation of 22 also matches the specified structure; the fragments specified for (E-22) (FIG. 2) also occur in a very similar form in the Z-configured 22 (FIG. 3). The most obvious mass-spectroscopic difference from the corresponding α,β-unsaturated alcohols is the favorable α,β bond fracture, which leads to a stronger fragment ion with m/z=135 (mass spectrum of 4; FIG. 4). In the case of allyl alcohols like 4, which was prepared from 18 by reduction with lithium aluminum hydride (in diethyl ether) the fragment with m/z=109 (cyclopentane system) resulting from allyl cleavage is much more pronounced than in the case of the corresponding β,γ-unsaturated alcohols (here: 22). Furthermore, in the case of the β,γ-unsaturated compounds a typical fragment ion with m/z=M$^+$−31 occurs (see FIG. 2) which shows distinctly less intensity in the corresponding α,β-unsaturated alcohols (FIG. 4). A further proof of constitution is given by the selective hydration which led to the analogous compounds with a saturated side chain; these compounds have been described in DEC No. 2,827,957. The specified criteria prove the structure of the new compounds of formula I. When lithium aluminum hydride/ether (0° C.) is used for reduction of the unsaturated aldehydes 17–20, deconjugation does not take place under customary reaction conditions.

The campholene aldehyde (1) can be produced from (+) or (−)-α pinene in an optically active form. Hence the C-1 side chain of compounds A can be of α- or β-configuration. In α-position (branching of the side chain) the deconjugated alcohols of the formula A exhibit an additional chiral center. The alcohols A are thus present as diastereomers; the stated Z/E isomerism may also be present. The β,γ-unsaturated alcohols given here as (Z) or (E) isomers may therefore also be present with the same geometry as diastereomers.

The derivatives of our invention can be used to contribute sandalwood notes or woody undertones to perfume compositions, perfumed articles such as solid or liquid anionic, cationic, nonionic or zwitterionic detergents, fabric softener compositions, fabric softener articles, fabric optical brighteners and other fabric conditioners. As olfactory agents the campholenyl derivatives of our invention can be formulated into or used as components of a "perfumed composition".

The term "perfumed composition" is used herein to mean a mixture of organic compounds including for example, alcohols other than the campholenyl derivatives of our invention, aldehydes, ketones, nitriles, ethers, lactones and frequently hydrocarbons which are admixed so that the combined odors of the individual components produce a pleasant or desired fragrance. Such perfumed compositions usually contain: (a) the main note of the "bouquet" or foundation-stone of the composition; (b) modifiers which round off and accompany the main note; (c) fixatives which include odorous substances which lend a particular note to the perfume throughout all stages of evaporation, and substances which retard evaporation; and (d) top-notes which are usually low-boiling, fresh-smelling materials.

In perfume compositions the individual component will contribute its particular olfactory characteristics, but the overall effect of the perfume composition will be the sum of the effect of each ingredient. Thus, the individual compounds of this invention, or mixtures thereof, can be used to alter the aroma characteristics of a perfume composition, for example, by highlighting or moderating the olfactory reaction contributed by another ingredient in the compositions.

The amount of campholenyl derivatives of our invention which will be effective in perfume compositions depends upon many factors including the other ingredients, their amounts and the effects which are desired. It has been found that perfume compositions containing as little as 1% of the campholenyl of our invention or even less and perfume compositions containing as much as 70% of the campholenyl derivatives of our invention can be used to impart interesting sandalwood notes or woody undertones to perfumed articles, perfumed compositions and colognes. Such perfumed articles include fabric softener compositions, dryer-added fabric softeners, cosmetic powders, talcs and solid or liquid anionic, cationic, nonionic or zwitterionic detergents. The amount employed can range up to 70% and will depend on considerations of cost, nature of the end product and the effect desired on the finished product and particular fragrance sought.

Thus, the campholenyl derivatives of our invention can be used alone or in a perfumed composition as an olfactory component in solid or liquid anionic, cationic, nonionic or zwitterionic detergents (including soaps), space odorants and deodorants, perfumes, colognes, toilet waters, bath salts, hair preparations such as lacquers, brillantines, pomades and shampoos, cosmetic preparations such as creams, deodorants, hand lotions and sunscreens; powders such as talcs, dusting powders, face powder and the like. When used as an olfactory component of a perfumed article such as a solid or liquid cationic, nonionic, anionic or zwitterionic detergent or of a cosmetic powder, as little as 0.01% of one or more of the campholenyl derivatives of our invention will suffice to provide interesting sandalwood notes or woody undertones. Generally, no more than 0.8% of the campholenyl derivatives of our invention is required.

In addition, the perfume compositions of our invention can contain a vehicle or carrier for the campholenyl derivatives of our invention alone or with other ingredients. The vehicle can be a liquid such as an alcohol, such as ethanol, a glycol such as propylene glycol, or the like. The carrier can be an absorbent solid such as a gum, or components for encapsulating the composition as by coacervation.

The present invention will be further described by reference to the following non-limiting examples.

EXAMPLE 1

Reduction of 2-ethyl-4-(2,2,3-trimethylcyclopent-3-en-1-yl)-but-2-en-al

Figure 5:
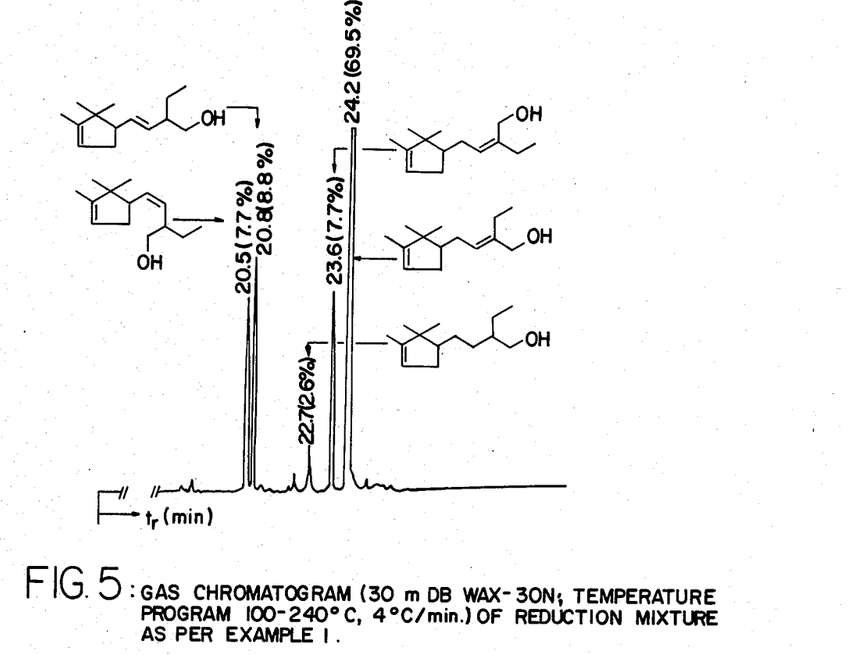
FIG. 5 shows the gas chromatogram of the reduction mixture from Example 1.

A solution of 15 g (0.395 mol) sodium borohydride and 0.15 g sodium hydroxide was dropped within one hour at 60° C. into a stirred solution of 275.5 g (1.25 mol) 2-ethyl-4-(2,2,3-trimethylcyclopent-3-en-1-yl)-but-2-en-al (18 prepared analogously with U.S. Pat. No. 4,052,341) in 250 g methanol. The reaction solution was left for another 30 minutes at 60° C. Then the methanol was distilled off. The residue was added to 200 g petrol ether (boiling point 50°–70° C.) and washed neutral with sodium chloride solution. The petrol ether was removed by distillation and the remaining raw product was fractionally distilled, a mixture of 2-ethyl-4-(2,2,3-trimethylcyclopent-3-en-1-yl)-but-3-en-1-ol (22, E+Z isomer), 2-ethyl-4-(2,2,3-trimethylcyclopent-3-en-1-yl)-butane-1-ol and 2-ethyl-4-(2,2,3-trimethylcyclopent-3-en-1-yl)-but-2-en-1-ol (4, E+Z isomer) being obtained; the yield was 203 g (78%); boiling point 110°–124° C./2 Pa; gas chromatogram FIG. 5; mass spectrum for E-22 FIG. 2, for Z-22 FIG. 3, and for E-4 FIG. 4.

A small part of the aforementioned distilled alcohol mixture was fractionally distilled again on a 1 m spinning band column, an analytic sample of pure 2-ethyl-4-(2,2,3-trimethylcyclopent-3-en-1-yl)-but-3-en-1-ol (22, E+Z isomer) being obtained: boiling point 111°–113° C./2 Pa; $^1$H-NMR spectrum FIG. 1. The reaction was performed analogously with the instructions given here at other temperatures and with other reaction times. The product mixtures were studies by gas chromatography (30 m DB WAX-30N; temperature program: 100°–240° C./min.). The results are shown in Table 1.

TABLE 1

| | Composition of the Reaction Products of 18 | | | | | | |
|---|---|---|---|---|---|---|---|
| | deconjugated alcohols | | saturated alcohol | conjugated alcohols | | | ratio |
| Conditions | % Z | % E | (%) | % Z | % E | ratio E/Z | conj./ deconj. |
| 15° C./5 min | 1,95 | 2,13 | 2,17 | 6,10 | 87,64 | 14,37 | 22,98 |
| 30° C./5 min | 1,92 | 2,14 | 2,55 | 5,99 | 87,39 | 14,59 | 23,00 |
| 40° C./5 min | 2,30 | 2,44 | 3,04 | 6,16 | 86,06 | 13,97 | 19,46 |
| 60° C./5 min | 3,71 | 4,05 | 3,23 | 6,48 | 82,51 | 12,73 | 11,45 |
| 30° C./1 h | 4,03 | 4,44 | 3,57 | 6,96 | 81,01 | 11,64 | 10,39 |
| 60° C./1 h | 7,95 | 9,12 | 2,68 | 7,98 | 72,27 | 9,06 | 4,70 |
| 10° C./45 min inverse | 2,66 | 2,95 | 2,66 | 6,98 | 84,75 | 12,15 | 16,33 |

EXAMPLE 2

Reduction of 2-methyl-4-(2,2,3-trimethylcyclopent-3-en-1-yl)-but-2-en-al

Figure 6:
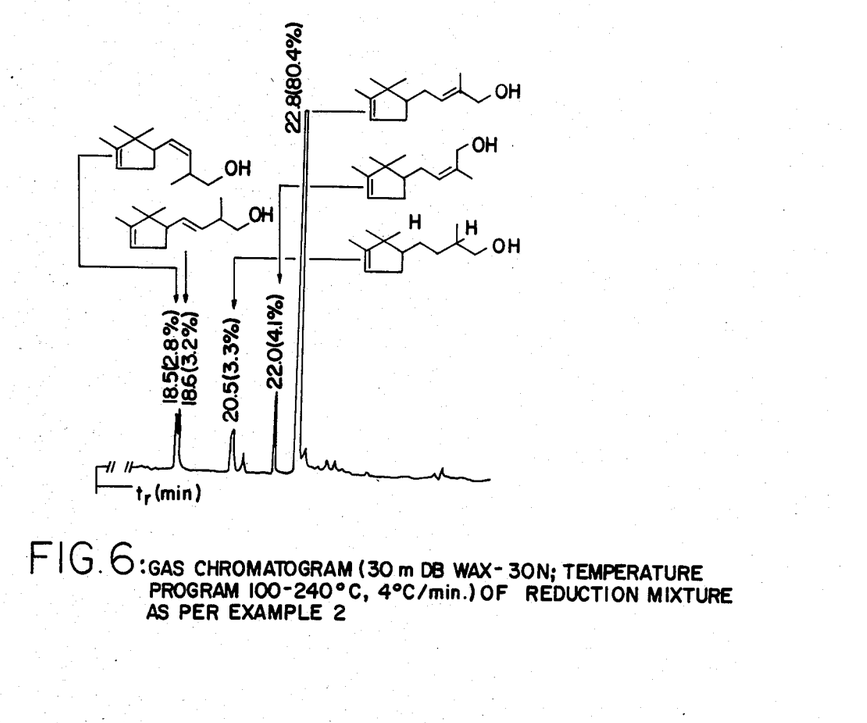
FIG. 6 shows the gas chromatogram of the reduction mixture from Example 2.

A solution of 10 g (0.236 mol) sodium borohydride and 0.1 g sodium hydroxide in 33 g water was dropped within one hour at 60° C. into a stirred solution of 153.6 (0.8 mol) 2-methyl-4-(2,2,3-trimethylcyclopent-3-en-1-yl)-but-2-en-al (17, prepared analogously with U.S. Pat. No. 4,052,341) in 160 g methanol. The reaction solution was left for another 30 minutes at 60° C. Then the methanol was distilled off. The residue was added to 150 g petrol ether (boiling point 50°–70° C.) and washed neutral with a sodium chloride solution. The petrol ether was removed by distillation and the remaining raw product was fractionally distilled, a mixture of 2-methyl-4-(2,2,3-trimethylcyclopent-3-en-1-yl)-but-3-en-1-ol (21, E+Z isomer), 2-methyl-4-(2,2,3-trimethylcyclopent-3-en-1-yl)-butan-1-ol and 2-methyl-4-(2,2,3-trimethyl-cyclopent-3-en-1-yl)-but-2-en-1-ol (3, E+Z isomer) being obtained; the yield was 115 g (74%; boiling point 96°–110° C./1.5 mm; gas chromatogram FIG. 6.

The reaction was carried out analogously with the instructions given here at other temperatures and with other reaction times. The mixtures produced were studied by means of gas chromatography (30 m DB WAX-30N; temperature program 100°–240° C., 4° C./min). The results are given in Table 2.

TABLE 2

Composition of the Reaction Products of 17

| Conditions | deconjugated alcohols E+ Z (%) | saturated alcohol (%) | conjugated alcohols % Z | conjugated alcohols % E | ratio E/Z | ratio conj./deconj. |
|---|---|---|---|---|---|---|
| 30° C./5 min | 2,07 | 3,19 | 3,97 | 90,78 | 22,89 | 45,82 |
| 60° C./5 min | 4,79 | 3,91 | 4,41 | 86,90 | 19,70 | 19,04 |
| 30° C./1 h | 2,14 | 3,16 | 4,10 | 90,60 | 22,09 | 44,34 |
| 60° C./1 h | 6,42 | 3,55 | 4,36 | 85,67 | 19,66 | 14,02 |

EXAMPLE 3

Mass-spectrometric Data of Compounds 3, 4 and 21–26

Compounds 3, 4 and 21–26 were analyzed by mass spectroscopy in a standard manner. The resulting data is shown in Table 3.

TABLE 3

| m/z | (%) | m/z | (%) | m/z | (%) |
|---|---|---|---|---|---|
| Z-21 | | | | | |
| 39 | 23 | 79 | 37 | 108 | 64 |
| 41 | 57 | 83 | 31 | 109 | 25 |
| 43 | 31 | 91 | 51 | 119 | 36 |
| 55 | 63 | 93 | 100 | 121 | 85 |
| 67 | 30 | 95 | 22 | 124 | 48 |
| 69 | 37 | 105 | 38 | 135 | 33 |
| 77 | 36 | 107 | 74 | M+: 194 | 6 |
| E-21 | | | | | |
| 41 | 43 | 79 | 32 | 108 | 57 |
| 43 | 30 | 83 | 20 | 109 | 22 |
| 55 | 56 | 91 | 44 | 119 | 38 |
| 67 | 30 | 93 | 100 | 121 | 45 |
| 69 | 34 | 105 | 28 | 124 | 36 |
| 77 | 28 | 107 | 83 | 135 | 26 |
| | | | | M+: 194 | 1 |
| Z-3 | | | | | |
| 39 | 21 | 79 | 40 | 107 | 54 |
| 41 | 51 | 81 | 27 | 108 | 100 |
| 43 | 53 | 84 | 41 | 109 | 62 |
| 53 | 20 | 91 | 40 | 119 | 29 |
| 55 | 36 | 93 | 87 | 121 | 54 |
| 67 | 72 | 95 | 47 | 122 | 25 |
| 77 | 27 | 105 | 32 | 161 | 28 |
| | | | | M+: 194 | 6 |
| E-3 | | | | | |
| 39 | 24 | 79 | 64 | 108 | 100 |
| 41 | 42 | 81 | 37 | 109 | 95 |
| 43 | 45 | 91 | 62 | 119 | 27 |
| 53 | 26 | 93 | 86 | 121 | 96 |
| 55 | 31 | 94 | 23 | 122 | 49 |
| 65 | 21 | 95 | 91 | 161 | 45 |
| 67 | 84 | 105 | 33 | 179 | 26 |
| 77 | 49 | 107 | 90 | M+: 194 | 12 |
| Z-22 | | | | | |
| 30 | 31 | 77 | 39 | 108 | 59 |
| 39 | 17 | 79 | 46 | 109 | 46 |
| 41 | 54 | 81 | 21 | 119 | 31 |
| 43 | 22 | 83 | 41 | 121 | 100 |
| 53 | 19 | 91 | 59 | 122 | 21 |
| 55 | 45 | 93 | 82 | 133 | 17 |
| 57 | 21 | 95 | 32 | 135 | 44 |
| 65 | 16 | 105 | 45 | 138 | 36 |
| 67 | 30 | 107 | 87 | 177 | 20 |
| | | | | M+: 208 | 4 |
| E-22 | | | | | |
| 29 | 15 | 69 | 45 | 108 | 71 |
| 31 | 29 | 77 | 40 | 109 | 42 |
| 39 | 19 | 79 | 41 | 119 | 39 |
| 41 | 51 | 81 | 21 | 121 | 100 |
| 43 | 20 | 83 | 36 | 122 | 22 |
| 53 | 18 | 91 | 61 | 133 | 18 |
| 55 | 44 | 93 | 89 | 135 | 44 |
| 57 | 22 | 95 | 34 | 138 | 39 |

TABLE 3-continued

| m/z | (%) | m/z | (%) | m/z | (%) |
|---|---|---|---|---|---|
| Z-21 | | | | | |
| 65 | 16 | 105 | 46 | 177 | 23 |
| 67 | 30 | 107 | 88 | M+: 208 | 5 |
| Z-4 | | | | | |
| 41 | 39 | 79 | 31 | 107 | 47 |
| 43 | 27 | 81 | 23 | 108 | 100 |
| 55 | 29 | 91 | 26 | 109 | 56 |
| 57 | 38 | 93 | 63 | 119 | 21 |
| 67 | 45 | 95 | 33 | 121 | 46 |
| 77 | 26 | 98 | 26 | 122 | 21 |
| | | | | M+: 208 | 5 |
| E-4 | | | | | |
| 27 | 14 | 77 | 36 | 108 | 98 |
| 29 | 28 | 79 | 52 | 109 | 97 |
| 30 | 11 | 81 | 42 | 119 | 29 |
| 39 | 23 | 82 | 15 | 121 | 100 |
| 41 | 56 | 83 | 13 | 122 | 43 |
| 43 | 49 | 91 | 45 | 123 | 11 |
| 53 | 24 | 93 | 79 | 135 | 18 |
| 55 | 45 | 94 | 16 | 161 | 13 |
| 57 | 81 | 95 | 77 | 175 | 27 |
| 65 | 15 | 98 | 15 | 177 | 11 |
| 67 | 82 | 105 | 25 | 193 | 15 |
| 69 | 18 | 107 | 80 | M+: 208 | 10 |
| Z-23 | | | | | |
| 31 | 28 | 83 | 41 | 109 | 47 |
| 40 | 65 | 91 | 53 | 110 | 31 |
| 43 | 29 | 93 | 71 | 119 | 41 |
| 55 | 67 | 95 | 35 | 121 | 100 |
| 67 | 35 | 105 | 35 | 122 | 28 |
| 77 | 31 | 107 | 82 | 135 | 47 |
| 79 | 39 | 108 | 73 | 152 | 33 |
| 81 | 26 | | | M+: 222 | 8 |
| E-23 | | | | | |
| 31 | 25 | 83 | 44 | 109 | 60 |
| 40 | 52 | 91 | 42 | 110 | 27 |
| 43 | 29 | 93 | 96 | 119 | 42 |
| 55 | 79 | 95 | 29 | 121 | 100 |
| 67 | 33 | 105 | 42 | 135 | 54 |
| 69 | 25 | 107 | 75 | 152 | 29 |
| 77 | 29 | 108 | 77 | 191 | 27 |
| 79 | 48 | | | M+: 222 | 10 |
| Z-25 | | | | | |
| 29 | 26 | 71 | 42 | 95 | 74 |
| 39 | 26 | 77 | 38 | 105 | 26 |
| 41 | 74 | 79 | 68 | 107 | 76 |
| 43 | 49 | 81 | 35 | 108 | 88 |
| 53 | 31 | 91 | 51 | 109 | 100 |
| 55 | 45 | 93 | 76 | 121 | 98 |
| 67 | 78 | 94 | 26 | 122 | 49 |
| | | | | M+: 222 | 10 |
| E-25 | | | | | |
| 39 | 22 | 77 | 27 | 107 | 35 |
| 40 | 51 | 79 | 49 | 108 | 38 |
| 43 | 54 | 81 | 30 | 109 | 100 |
| 55 | 41 | 91 | 27 | 119 | 24 |
| 57 | 22 | 93 | 65 | 121 | 43 |
| 67 | 49 | 94 | 22 | 122 | 22 |
| 69 | 22 | 95 | 76 | 189 | 22 |
| 71 | 60 | | | M+: 222 | 8 |
| Z-24 | | | | | |
| 31 | 28 | 81 | 30 | 109 | 92 |
| 41 | 72 | 83 | 57 | 112 | 34 |
| 43 | 55 | 91 | 70 | 119 | 49 |
| 55 | 98 | 93 | 89 | 121 | 100 |
| 67 | 40 | 95 | 51 | 122 | 30 |
| 69 | 47 | 105 | 57 | 133 | 30 |
| 77 | 43 | 107 | 77 | 135 | 62 |
| 79 | 45 | 108 | 87 | M+: 222 | 11 |
| E-24 | | | | | |
| 31 | 28 | 77 | 44 | 107 | 74 |
| 39 | 26 | 79 | 50 | 108 | 80 |
| 41 | 76 | 81 | 28 | 109 | 98 |
| 43 | 46 | 83 | 52 | 112 | 32 |
| 53 | 26 | 91 | 57 | 119 | 50 |
| 55 | 100 | 93 | 85 | 121 | 98 |
| 67 | 43 | 95 | 48 | 133 | 26 |
| 69 | 44 | 105 | 57 | 135 | 63 |

TABLE 3-continued

| m/z | (%) | m/z | (%) | m/z | (%) |
|---|---|---|---|---|---|
| Z-21 | | | | | |
| | | | | M+: 222 | 7 |
| Z-26 | | | | | |
| 41 | 37 | 81 | 19 | 108 | 100 |
| 43 | 37 | 91 | 22 | 109 | 52 |
| 55 | 33 | 93 | 61 | 112 | 16 |
| 67 | 36 | 95 | 31 | 119 | 18 |
| 69 | 19 | 105 | 18 | 121 | 42 |
| 77 | 24 | 107 | 39 | 122 | 17 |
| 79 | 30 | | | M+: 222 | 4 |
| E-26 | | | | | |
| 39 | 28 | 71 | 26 | 95 | 68 |
| 41 | 68 | 77 | 40 | 107 | 75 |
| 43 | 60 | 79 | 75 | 108 | 100 |
| 53 | 28 | 81 | 39 | 109 | 95 |
| 55 | 49 | 91 | 52 | 121 | 93 |
| 67 | 65 | 93 | 83 | 122 | 40 |
| 69 | 26 | 94 | 28 | M+: 222 | 6 |

EXAMPLE 4

Perfume Base of the Sweet-Herby Type

| | |
|---|---|
| 2,2-dimethyl-3-phenyl-propanol (muguet alcohol, DE PS 3 139 358) | 50 |
| Oil of lavender, French | 15 |
| Hyssop oil, Spanish | 10 |
| Oak moss extract, 50% in dipropylene glycol | 10 |
| Dihydromyrcene alcohol | 5 |
| Oil of rosemary, Spanish | 5 |
| Product from Example 2 (21 + 3) | 5 |
| | 100 |

This base, which contains a relatively high proportion of the product from Example 2, has an attractive fresh and sweet-herby harmony with a distinct but soft woody note.

EXAMPLE 5

Perfume Base of the Woody-Spicy Type

| | |
|---|---|
| Mahogonate | 150 |
| Vetiveryl acetate | 100 |
| Muscogene | 100 |
| Caryophyllenol | 100 |
| Patchouli oil | 50 |
| 2,2-dimethyl-5-phenyl propanol (muguet alcohol, DE PS 3 139 358) | 50 |
| Musk ketone | 30 |
| Oak moss extract, 50% | 20 |
| Labdanum resinoid, 50% | 20 |
| Myrrh resinoid | 10 |
| Oil of pepper | 5 |
| Nutmeg oil | 5 |
| Cistus oil | 5 |
| Eugenol | 5 |
| | 650 |

This perfume base has a woody-spicy character with musk aspects. When 100 parts of compound 4 (DE OS No. 1 922 391) are added, a rounding out with simultaneous accentuation of sweetish-woody aspects is found. If 100 parts of compound 22 are added, the scent is more harmonious, with accentuation of the woody-animal aspects. The introduction of 100 parts of the product from Example 1 (22+4) yields a balanced composition with a sandalwood aspect.

EXAMPLE 6

A Perfume Oil of the Flowery Type

| | a | b | c |
|---|---|---|---|
| Citronellol | 20 | 20 | 20 |
| Phenyl ethyl alcohol | 170 | 170 | 170 |
| Indol, 50% in dipropylene glycol | 5 | 5 | 5 |
| Isoeugenol | 5 | 5 | 5 |
| Benzyl acetate | 30 | 30 | 30 |
| Linalool | 40 | 40 | 40 |
| Terpineol | 240 | 240 | 240 |
| 2,2-dimethyl-3-phenyl-propanol-1 (muguet alcohol, DE·PS 3 139 358) | 200 | 200 | 200 |
| Cinnamic alcohol | 40 | 40 | 40 |
| Citronellyl acetate | 20 | 20 | 20 |
| Frambinone | 15 | 15 | 15 |
| 1,4-dimethyl-8-hydroximino-bicyclo-[3.2.1]octane (DE PS 3 129 934) | 60 | 60 | 60 |
| Hydroxycitronellal | 25 | 25 | 25 |
| Compound 4 (DE OS 1 922 391) | 20 | — | — |
| Compound 22 | — | 20 | — |
| Product from example 1 (22 + 4) | — | — | 20 |
| | 890 | 890 | 890 |

The mixture a has a well-balanced flowery scent of the type lily-of-the-valley/white lily. In mixture b, which contains the new compound 22 instead of allyl alcohol 4, an emphasis of the fresh note is found. Mixture c, in turn, has a harmonious flowery scent with a slight accentuation of woody aspects.

What is claimed is:

1. A compound having the formula I wherein R may be methyl, ethyl, propyl, isopropyl or butyl, the wavy line characterizes geometrical isomers and the broken lines characterize stereoisomers.

2. The compound of claim 1 wherein R is methyl.
3. The compound of claim 1 wherein R is ethyl.
4. The compound of claim 1 wherein R is propyl.
5. The compound of claim 1 wherein R is isopropyl.
6. A method for producing a compound as described in claim 1 which comprises:
   (a) condensing campholene aldehyde and R—$CH_2$—CHO, where R is defined as in claim 1, catalyzed by alkali hydroxides or alcoholates, and
   (b) reducing in an alkaline environment the resulting $\alpha,\beta$-unsaturated aldehydes using sodium borohydride at temperatures of 10°–80° C.
7. The method of claim 6 wherein the temperature in step (b) is 30°–60° C.
8. A perfume composition containing as an active perfume ingredient an amount of at least one compound of formula I according to claim 1 sufficient to impart sandalwood notes or woody undertones thereto.
9. The perfume composition of claim 8 wherein said active perfume ingredient comprises two or more compounds of formula I.
10. An artificial essential oil of sandalwood notes or woody undertones, which comprises having added thereto an amount of at least one compound of formula I according to claim 1 sufficient to impart sandalwood notes or woody undertones thereto.

11. The artificial essential oil of claim 10 wherein two or more compounds of formula I are added.

12. A process for augmenting or enhancing the aroma of a perfume or cologne composition comprising the step of adding to a perfume or cologne base an aroma augmenting or enhancing quantity of a product containing at least one compound having the structure wherein R may be methyl, ethyl, propyl, isopropyl or butyl, the wavy line characterizes geometrical isomers and the borken lines characterize stereoisomers.

13. The process of claim 12 wherein said product comprises two or more compounds of formula I.

14. The method of claim 6 which further comprises the step of
 (c) separating the compound from the resulting mixture by distillation.

15. The method of claim 14 wherein the temperature in step (b) is 30°–60° C.

16. A perfume composition containing as an active perfume ingredient an amount of a reduction mixture containing at least 1% of a compound of formula I according to claim 1 sufficient to impart sandalwood notes or woody undertones.

17. An artificial essential oil of sandalwood notes or woody undertones which comprises having added thereto an amount of a reduction mixture containing at least 1% of a compound of formula I according to claim 1 sufficient to impart sandalwood notes or woody undertones thereto.

* * * * *